United States Patent [19]

Hölzl

[11] 4,365,505

[45] Dec. 28, 1982

[54] APPARATUS FOR DETERMINING THE GAS CONTENT OF A LIQUID

[75] Inventor: Emil Hölzl, Munich, Fed. Rep. of Germany

[73] Assignee: Krauss-Maffei Aktiengesellschaft, Munich, Fed. Rep. of Germany

[21] Appl. No.: 165,397

[22] Filed: Jul. 2, 1980

[30] Foreign Application Priority Data

Jul. 18, 1979 [DE] Fed. Rep. of Germany ....... 2929013

[51] Int. Cl.³ .................... G01N 7/00; G01N 33/44
[52] U.S. Cl. ...................................................... 73/19
[58] Field of Search .................. 73/19, 599; 264/40.1, 264/50

[56] References Cited

U.S. PATENT DOCUMENTS

| | | | |
|---|---|---|---|
| 3,486,370 | 12/1969 | Chedeville et al. | 73/599 X |
| 3,654,072 | 4/1972 | Massa | 73/599 X |
| 3,738,154 | 6/1973 | Henry . | |
| 4,089,206 | 5/1978 | Raffel et al. | 73/19 |
| 4,208,906 | 6/1980 | Robert | 73/597 X |
| 4,255,088 | 3/1981 | Newton et al. | 73/19 |

FOREIGN PATENT DOCUMENTS

| | | |
|---|---|---|
| 2455257 | 5/1976 | Fed. Rep. of Germany . |
| 2255159 | 7/1975 | France . |
| 2325922 | 4/1977 | France . |
| 2390721 | 12/1978 | France . |

*Primary Examiner*—James J. Gill
*Attorney, Agent, or Firm*—Karl F. Ross

[57] ABSTRACT

Disclosed are a method of and an apparatus for determining entrained gas content in a liquid, especially a liquid synthetic-resin component adapted to form a foamed or cellular synthetic-resin body. Pressure pulses are applied to the liquid and pressure oscillations therein are detected, the amplitude Δp and/or the phase position of a peak being detected and evaluated to give the gas content. The determination may be used to control the addition of the gas to the liquid and/or can be displayed to permit operator control of the system.

6 Claims, 2 Drawing Figures

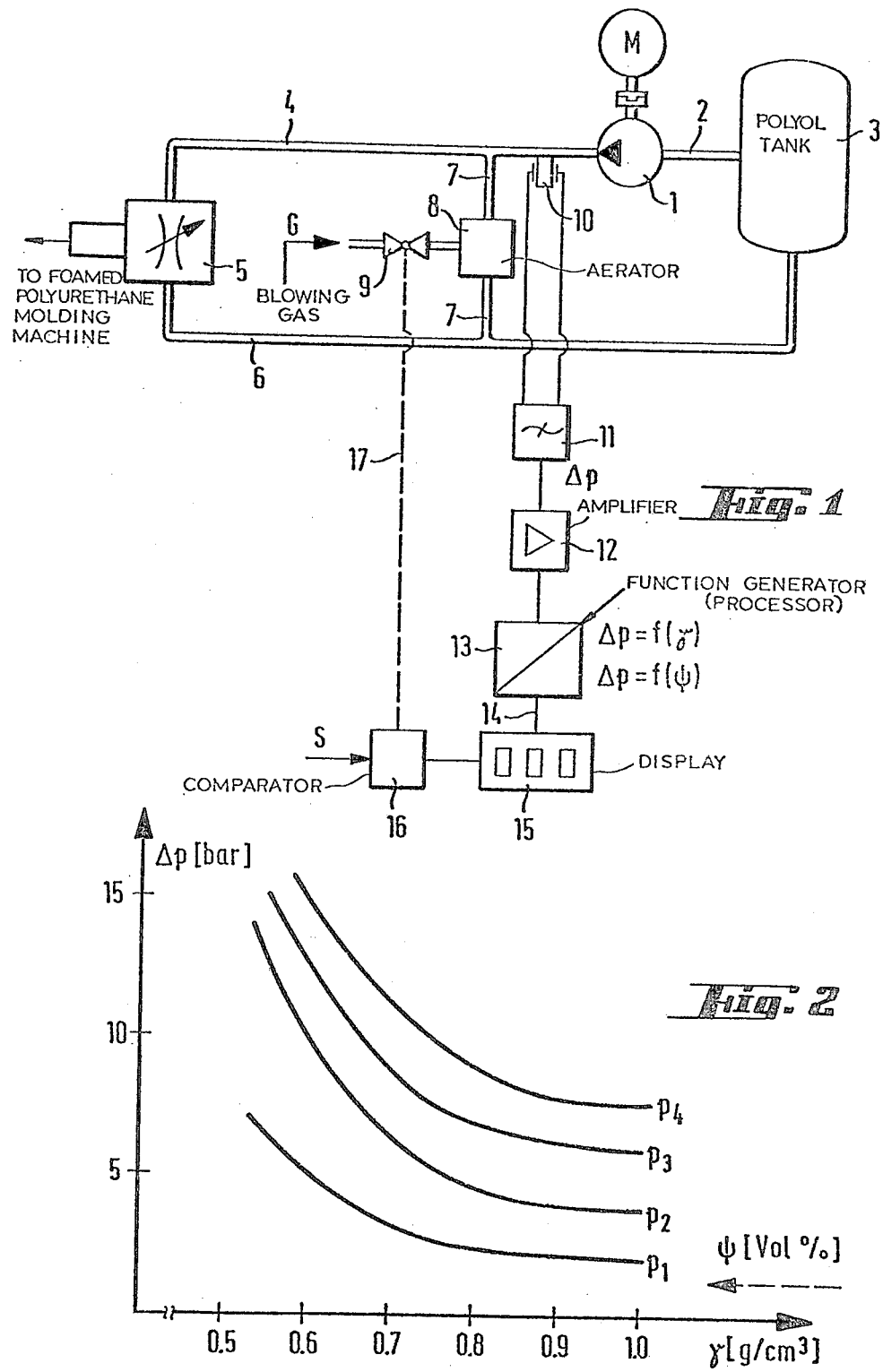

APPARATUS FOR DETERMINING THE GAS CONTENT OF A LIQUID

FIELD OF THE INVENTION

My present invention relates to an apparatus for determining the gas content of a liquid and, more particularly, for determining the quantity of gas entrained by and dissolved in a liquid component of a synthetic resin for the production of foamed or cellular synthetic-resin articles.

BACKGROUND OF THE INVENTION

It is known that gas-charged liquid components of synthetic resin can be used in the production of foamed or cellular articles in which the gas phase can expand, at least in part, to produce cells or cavities in the body when it sets or hardens.

In the production of foamed polyurethanes, for example, a gas, constituting a foaming agent, can be incorporated in the liquid polyol component which is combined with diisocyanate or polyisocyanate in a mixing chamber to form a reactive mixture which, upon entry into the mold, allows the gas to expand and bring about a foamed structure.

With processes utilizing the two-phase system polyol/air for the production of polyurethane foams, the foaming action is a function of the quantity of air or gas bubbles which are included in the mixture and which derive from air or gas entrained with the polyol component.

The quality of the product depends upon the quantity of air entrained with the polyol component and the constancy of this quantity.

To reliably maintain a given set of quality standards for foamed synthetic articles, it is desirable to be able to determine accurately the degree to which the liquid component is charged with the gas and to hold it constant within a narrow range.

The problem has been attacked by other methods and devices in a generally unsatisfactory manner because monitoring of the gas content is usually performed upon a return of bypassed flow of the gas-entraining component.

A liquid sample is taken from the recycled region at a pressure substantially lower than the pressure in the inlet side or high-pressure side of the device.

The measuring device is of the membrane type and the results must be corrected in accordance with approximations for the specific gas/liquid characteristics of the liquid synthetic-resin component at the high-pressure side.

Apart from the relative imprecision of the measurement, the fact that it is also discontinuous is a paramount disadvantage, not only for the uniformity of the quality characteristics and the stability thereof over long periods, but because of the nonvariability of the gas-charging degree.

OBJECTS OF THE INVENTION

It is the principal object of my present invention to provide an improved system for measuring the extent to which a liquid entrains a gas, especially a liquid synthetic-resin component entraining air, whereby the disadvantages of earlier systems are avoided.

Another object of the invention is to provide a system for the purposes described which operates on the high pressure side with high-precision.

Yet another object of the invention is to provide a relatively simple, easily controlled apparatus for the detection of a gas phase in a liquid, especially a foaming agent in a liquid polyol.

SUMMARY OF THE INVENTION

This invention is based upon my discovery that a unique property of synthetic-resin fluid can allow detection of the gas concentration in the liquid phase, practically continuously, without sampling, and without complicated analytical apparatus or techniques.

More specifically, I have found that the pressure oscillation or pulse transmission through the traveling liquid component, containing dissolved or mechanically entrained gas (especially gaseous foaming agents), varies as a function of the gas concentration which appears to affect the compressibility of the liquid.

According to the invention, therefore, along the path of a gas-entraining liquid component, preferably at the high-pressure side of the system, pressure pulses or oscillations are applied to the liquid stream. These pulses or pressure oscillations are detected by a transducer downstream of the pulse-generating or oscillation-generating devices, and the amplitude of the measured variations and/or the phase position of the corresponding parts of the measured oscillation, e.g. peaks or troughs, gives rise to an intermediate signal indicative of the pressure-propagating characteristics of the liquid/gas mixture. This intermediate signal is then converted by electronic processing means, preprogrammed with one or more characteristic curves, into an output signal corresponding to a predetermined parameter which represents the gas concentration in the liquid.

According to a feature of the invention, the liquid is set into harmonic oscillation, e.g. by a metering or feed pump which has a pulsed output. It is the pulses of this device which, when transmitted through the liquid, are measured so that phase shifting of the measured values and/or the amplitude of the signals can indicate the gas concentration.

Advantageously, the generated output signal is compared with a reference signal and the result is used to control the feed of air to the liquid. The characteristic curves of the processing means may plot the amplitude $\Delta p$ as a function of the density $\gamma$ and/or a direct measure $\psi$ of the proportion of the gas in the gas-entraining liquid component. These characteristic curves are plotted for different mean pressures $p_1$, $p_2$ etc. selected to suit the particular molding parameters.

According to still another feature of the invention, the density $\gamma$ or the percentage $\psi$ of the gas component, transformed by the transducer, is received by an indicator or display for permitting visual ascertainment of the measurement.

The pressure transducer or sensor can be a piezoelectric element or a strain-gauge strip adapted to generate electrical output peaks representing the passage of pressure surges to the sensor. This pressure sensor may also deliver a mean pressure value to the processor representing the actual operating pressure. When the operating pressure coincides with one of the values $p_1$, $p_2$, etc., for which the processor has been preprogrammed, the output of the processor can read directly in terms of the percentage of gas in the liquid corresponding to the instantaneous value of the amplitude $\Delta p$. When the operating pressure is between values $p_1$, $p_2$, etc., the processor can be programmed to extrapolate the percentage gas content from the measured value of $\Delta p$. Alternatively, or in addition, the device can be provided with a switch or circuit arrangement for selecting among the characteristic curves $p_1$, $p_2$, etc.

The processor, which thus acts as a function generator providing a given response to an input $\Delta p$ and operating pressure p, can be either a digital or an analog circuit and can be provided with a digital or analog display from which the operator can readily ascertain the degree to which the liquid is charged with gas. Furthermore, the function generator can be connected to a comparator circuit so that the latter is fed with an instantaneous actual-value signal representing the density or gas proportion in the liquid and with a set-point signal representing the desired value, the resulting error signal controlling the introduction of gas into the liquid.

As a result, the automatic control circuit can maintain fluctuations in the degree of charging of the gas automatically within narrow limits.

BRIEF DESCRIPTION OF THE DRAWING

The above and other features of the present invention will become more readily apparent from the following description, reference being made to the accompanying drawing in which:

FIG. 1 is a flow diagram illustrating principles the of the present invention; and FIG. 2 is a graph showing characteristic curves as may be utilized in the practice of the invention.

SPECIFIC DESCRIPTION

The drawing shows the principles of the invention as applied to a system for charging a polyol with gas and feeding the polyol as a liquid component to a mixing valve provided with a plunger so that, when mixing is precluded, the liquid component is recirculated through a bypass in the plunger and returns to the container. Systems of this type are found in U.S. Pat. No. 3,799,199 and No. 3,706,515.

Omitted from the drawing is the system for recirculating the other component adapted to form the mixture, e.g. a diisocyanate or polyisocyanate, when the mixture is to produce a foamed or cellular polyurethane.

Thus, in FIG. 1, there is shown a positive-displacement pump 1 which is connected at its suction side 2 to a storage vessel 3, namely, a tank, for a liquid synthetic-resin component to be charged with gas. This liquid can be pure or previously charged with gas and is, as has been noted, preferably a polyol for the production of a polyurethane.

The pump 1 is driven by a motor M and displaces the liquid through a high-pressure line 4 to a mixing unit or chamber 5 of the type described, the return flow being carried by the line 6 back to the tank 3.

The pump 1 is of the pulsed-displacement type, e.g. a peristaltic pump, so that surges of pressure are developed in the liquid in line 4.

The high-pressure line 4 and the return line 6 are also connected by a line 7 in which there is provided a gas-charging chamber which can be formed with an aeration block supplied with the expanding or blowing agent, e.g. air, by a gas-pressure source G which can be an air compressor. A valve 9, electrically controlled by the automatic control circuit described hereinafter is disposed between the gas source G and the charging unit 8.

The high-pressure line 4 is also provided with a pressure sensor 10, for example, a piezoelectric element or a strain-gauge bridge, whose output is applied to a signal modifier 11, e.g. a filter, transforming the output signals of the pressure/electric transducer 10 into an analog or digital intermediate signal representing the pressure $\Delta p$. For example, this unit can pass electrical signals representing peak values of the pressure, corresponding to $\Delta p$.

The signal modifier 11 delivers that intermediate signal to an amplifier 12 which is connected, in turn, to a processor 13, namely a function generator (in the analog case) or a digitizer (in the digital case) which compares the received signal with previously stored values to generate an output signal at 14 which represents the corresponding value of $\gamma$, i.e. the density of the liquid, or $\psi$, the percentage gas content.

In both the analog and the digital case, the unit 13 is preprogrammed with at least one characteristic curve (similar to those of FIG. 2) by which, on an empirical basis, the relationship between $\Delta p$ and the values $\psi$ or $\gamma$ have been plotted.

When a plurality of characteristic curves are plotted for various operating pressures $p_1$, $p_2$, $p_3$ or $p_4$, the unit 13 can be switched to respond to the curve for the actual operating pressure or a further output can be derived from transducer 10 representing the mean pressure which, of course, will then correspond to the operating pressure and can be used to select among the effective stored characteristic curves in the memory of the signal processor 13.

The electrical signal at line 14 thus is proportional to the density $\gamma$ or the volume percent $\psi$ of gas in the liquid downstream of the pump 1 which here functions as a pressure-pulse generator along the liquid line.

This signal is applied to a display 15, which can be of the analog or digital type, affording a direct readout of the density or volume percent for the information of the machine operator.

In addition, this signal is supplied as an actual-value signal to a comparator 16 which is also supplied with a set-point input S representing the desired proportion of gas in the liquid, any deviation of the instantaneous-value signal from the set-point value resulting in an error or deviation signal applied as represented by line 17 to the valve 9 to control the addition of gas to the liquid.

Thus a highly rapid and precise control can be obtained of the gas content of the liquid, thereby maintaining the degree of charging of the liquid constant between narrow limits as is especially important in the production of high-quality foamed synthetic-resin articles.

FIG. 2 shows the relationship employed in accordance with the principles of the present invention. In this FIGURE, the amplitude of the pressure fluctuations $\Delta p$ has been plotted in bar, along the ordinate, against $\gamma$ and $\psi$, respectively, in $g/cm^3$ and volume percent. Obviously, as the density $\gamma$ increases, the proportion of gas entrained in the liquid drops and hence values of the volume percent and density increases inversely to one another.

FIG. 2 shows four characteristic curves for selected operating pressure $p_1$, $p_2$, $p_3$, and $p_4$. In each case, the greater the volume percent of gas in the liquid and the lower its density, the greater are the pressure fluctuations (value of Δp) which can be sustained by the liquid column downstream of the pump (or other pressure-pulse generator) because of the increased compressibility of the mass within the pipe and increased mass which can be set harmonically into motion by the pressure pulses. Thus each curve has the appearance of the law of motion of a double-mass oscillator.

Actual values have been represented in FIG. 2, by way of specific example, with the pressures $p_1=50$ bar, $p_2=100$ bar, $p_3=150$ bar and $p_4=200$ bar for a liquid component consisting of polyols and air as the gas. These curves, determined empirically, are preprogrammed into the processor 13. When the pump is of the continuous-pressure type, i.e. is incapable of functioning as a pressure-pulse generator, a separate periodically operated pulse generator, such as a cylinder with a reciprocating piston, may be used.

In the latter case, as a substitute for Δp values, one may measure the phase shift of the pressure pulse, e.g. by monitoring the time between the attainment of a pressure maximum at the pulse generator and the attainment of a pressure maximum at the pressure sensor 10. This time, which increases with increasing gas content of the liquid and decreasing density, can also be represented by values along the ordinate equivalent to the Δp values given.

I claim:

1. An apparatus for determining the gas content of a liquid, comprising:

pump means for generating a pulsating stream of a gas-containing liquid in a flow channel;

detector means disposed at said flow channel downstream of said pump means and responsive to the pulsations in the pulsating stream produced by said pump means for generating an intermediate signal indicative of the pressure-propagating characteristics of the liquid/gas mixture flowing in said channel;

electronic processing means connected to said detector means and preprogrammed with at least one characteristic curve for converting said intermediate signal into an output signal corresponding to a predetermined parameter representing the proportion of gas in said liquid; and a load responsive to said output signal connected to said processing means.

2. An apparatus as defined in claim 1 wherein said load comprises display means for visually indicating the magnitude of said parameter.

3. An apparatus as defined in claim 1 wherein said channel is connected to an adjustable source of gas to be continuously introduced into the liquid, said load comprising comparison means connected to a control input of said source for varying the rate of gas introduction to compensate for deviations of said output signal from a given set-point value.

4. An apparatus as defined in claim 1, 2 or 3 wherein said processing means is switchable among a plurality of stored characteristic curves plotted for different mean pressures.

5. The apparatus defined in claim 1, 2 or 3 wherein said detector means is a piezoelectrical element.

6. The apparatus defined in claim 1, 2 or 3 wherein said detector means is a strain-gauge element.

* * * * *